(12) United States Patent
Ogura

(10) Patent No.: US 6,592,819 B1
(45) Date of Patent: Jul. 15, 2003

(54) MICROARRAY CHIP MANUFACTURING APPARATUS

(75) Inventor: Nobuhiko Ogura, Kaisei-machi (JP)

(73) Assignee: Fuji Photo Film Co., Ltd., Kanagawa-ken (JP)

( * ) Notice: Subject to any disclaimer, the term of this patent is extended or adjusted under 35 U.S.C. 154(b) by 208 days.

(21) Appl. No.: 09/672,822

(22) Filed: Sep. 29, 2000

(30) Foreign Application Priority Data

Sep. 30, 1999 (JP) .............................. 11-279090

(51) Int. Cl.[7] .............................. B32B 5/02; B01L 3/02
(52) U.S. Cl. .................... 422/63; 422/50; 422/68.1; 422/100
(58) Field of Search ................. 422/100, 68.1, 422/63, 50; 700/218; 436/180

(56) References Cited

U.S. PATENT DOCUMENTS

| | | | |
|---|---|---|---|
| 5,061,449 A | * | 10/1991 | Torti et al. .................. 422/100 |
| 6,024,925 A | * | 2/2000 | Little et al. .................. 422/100 |
| 6,228,659 B1 | * | 5/2001 | Kowallis et al. ............ 436/180 |
| 6,255,119 B1 | * | 7/2001 | Baier ........................ 436/180 |
| 6,347,259 B1 | * | 2/2002 | Goldenberg et al. ........ 700/218 |

* cited by examiner

Primary Examiner—Jill Warden
Assistant Examiner—Brian Sines
(74) Attorney, Agent, or Firm—Sughrue Mion, PLLC

(57) ABSTRACT

A microarray chip manufacturing apparatus includes a plurality of picking pins which pick specific binding substances linearly or two-dimensionally arranged at first spaces and spot the specific binding substances onto a flat chip at second spaces narrower than the first spaces. The picking pins are movable so that the spaces among the picking pins can be switched between the first spaces and the second spaces, and a space switching mechanism switches the spaces among the picking means to the first spaces when the picking means pick the specific binding substances and to the second spaces when the picking means spot the specific binding substances onto the chip.

8 Claims, 6 Drawing Sheets

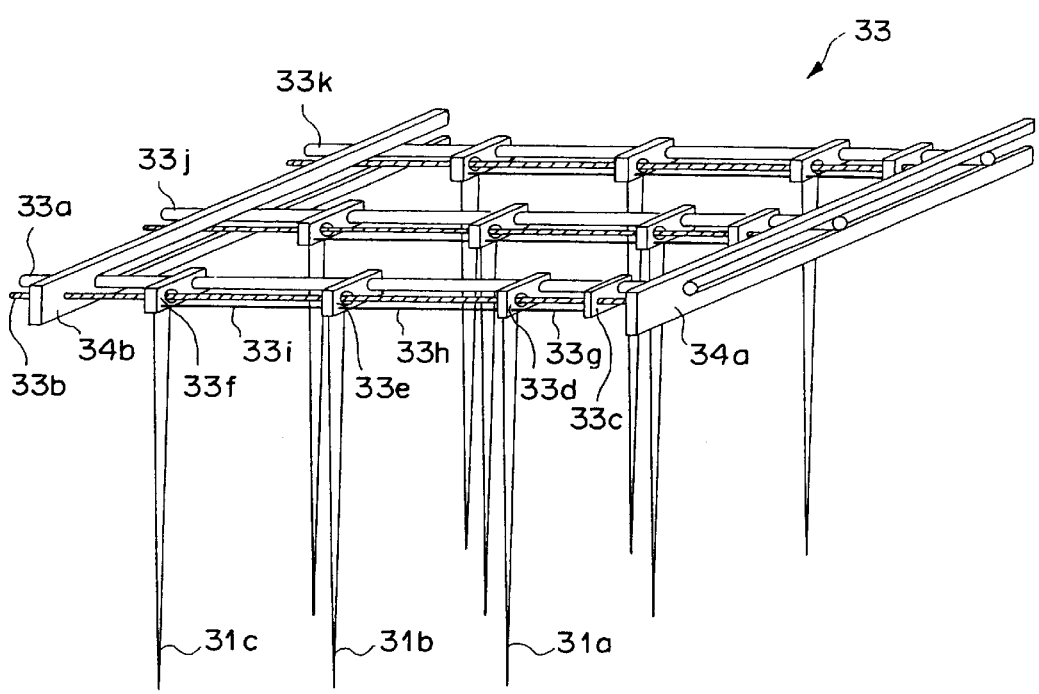
F I G . 2

F I G . 5
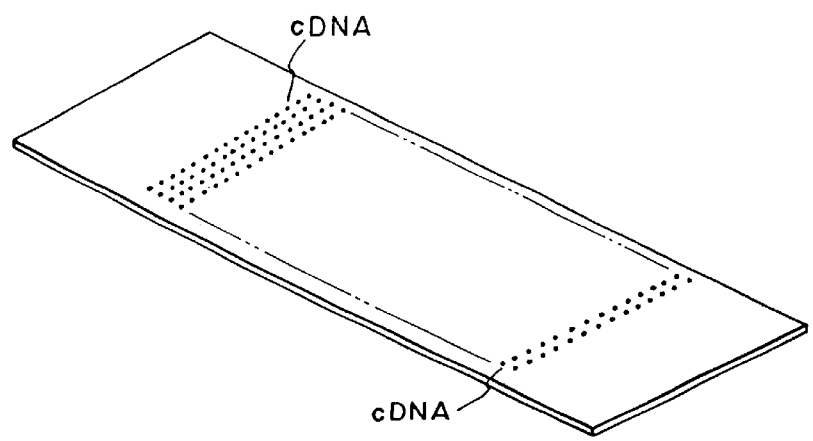
F I G . 6
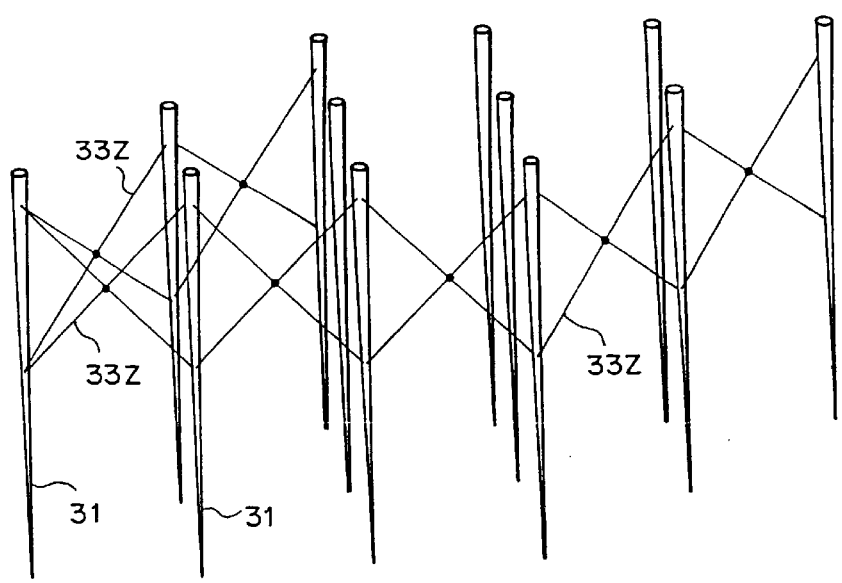

MICROARRAY CHIP MANUFACTURING APPARATUS

BACKGROUND OF THE INVENTION

1. Field of the Invention

This invention relates to an apparatus for manufacturing microarray chip for use in DNA analysis, immunological analysis, and the like, and more particularly to an improvement in the structure for spotting specific binding substances onto a chip.

2. Description of the Related Art

Recently, genetic engineering has exhibited rapid progress, and the human genome project for decoding the base sequence of human genomes which amount to 100,000 in number is progressing. Further, enzyme immunoassay, fluorescent antibody technique and the like utilizing antigen-antibody reactions have been used in diagnoses and studies, and studies for searching DNAs which affect genetic diseases are now progressing. In such a situation, a microarray technique is now attracting attention.

In the microarray technique, a microarray chip (sometimes called DNA chip) comprising a plurality of known cDNAs (an example of specific binding substances) spotted in a matrix on a chip such as of a membrane filter or a slide glass at a high density (at intervals of not larger than several hundred $\mu$m) as shown in FIG. 5 is used and DNAs (an example of organism-originating substances) taken from cells of a normal person A and labeled with a fluorescent dye a and DNAS taken from cells of a genetic-diseased person B and labeled with a fluorescent dye b are dropped onto the microarray chip by pipettes or the like, thereby hybridizing the DNAS of the specimens with the cDNAs on the microarray chip. Thereafter, exciting light beams which respectively excite the fluorescent dyes a and b are projected onto the cDNAS by causing the exciting light beams to scan the microarray chip and fluorescence emitted from each of the cDNAS is detected by a photodetector. Then the cDNAs with which the DNAs of each specimen are hybridized are determined on the basis of the result of the detection, and the cDNAs with which the DNAs of the normal person A are hybridized and those with which the DNAs of the diseased person B are hybridized are compared, whereby DNAs expressed or lost by the genetic disease can be determined. This information contributes to gene therapy.

The number of specific binding substances such as cDNAs have been spotted on a chip such as of a membrane filter or a slide glass at a high density by means of a microarray chip manufacturing apparatus(a spotter or an arrayer) as shown in FIG. 3.

In the microarray chip manufacturing apparatus shown in FIG. 3, there is used a microtiter plate 10 having a number of specific binding substance holes 10a which are two-dimensionally arranged at pitches P larger than pitches at which the specific binding substances 11 are to be spotted onto a chip 20. The specific binding substance holes 10a are respectively filled with the specific binding substances 11. The microarray chip manufacturing apparatus comprises a spot head 30 provided with a plurality of, e.g., two×two, specific binding substance picking pins 31 which are arranged at the same pitches as the pitches P at which the specific binding substance holes 10a of the microtiter plate 10 are arranged, and a means for moving the spot head 30.

The microtiter plate 30 is about 8 cm×12 cm in size and the number of the specific binding substance holes 10a on the microtiter plate 30 is generally in the range of 8×12 (=96) to 32×48 (=1536). To the contrast, the chip 20 on which the specific binding substances 11 are spotted is about 2 cm×2 cm in size operation of a microarray chip manufacturing apparatus which spots 96 specific binding substances 11 onto a chip 20 by the use of a microtiter plate 10 having 8×12 specific binding substance holes 10a will be described, hereinbelow.

First the spot head 30 is moved to a position where the four picking pins 31 are aligned with the upper left four (2×2) specific binding substance holes 10a and then moved downward so that the picking pins 31 are inserted into the respective specific binding substance holes 10a and the specific binding substances 11 therein adheres to the picking pins 31. Thereafter, the spot head 30 is moved upward and to the chip 20 and then moved downward so that the picking pins 31 are brought into contact with the chip 20, whereby the specific binding substances 11 on the respective picking pins 31 are spotted onto the chip 20 as shown in FIG. 4A. In FIG. 4A and the following FIGS. 4B to 4D, the small circles indicated at × show the specific binding substance holes 10a into which the picking pins 31 are inserted at that time. When a plurality of microarray chips are to be manufactured, the same procedure is repeated the like number of times.

Then the specific binding substances 10a in the four holes 10a on the right side of the holes 10a the specific binding substances 11 in which are initially spotted (i.e., third and fourth holes 10a in the uppermost line as numbered from the left and third and fourth holes 10a in the second uppermost line as numbered from the left) are picked. At this time, since the specific binding substances 11 in the respective holes 10a are generally different from each other, it is necessary to clean the pins 31 by ultrasonic cleaning and to dry the same prior to picking the next specific binding substances 11 in order to prevent the preceding specific binding substances 11 from mingling with the next specific binding substances 11. After cleaning and drying the pins 31, the pins 31 are inserted into the next four holes 31 and the spot head 30 are moved so that the specific binding substances 11 in the holes 31 are spotted onto the chip 20 on the right side of the preceding spots at distances therefrom smaller than the distance (pitch) P between the pins 31 (e.g., P/6) as shown in FIG. 4B.

After these procedure (including picking, spotting, cleaning and drying) is repeated six times and the specific binding substances 11 in the upper right four holes 10a (i.e., first and second holes 10a in the uppermost line as numbered from the right and first and second holes 10a in the second uppermost line as numbered from the right) are spotted onto the chip 20, twenty-four specific binding substances 11 are spotted onto the chip 20 in two lines as shown in FIG. 4C.

Thereafter, the specific binding substances 11 in the holes 10a on the third and fourth lines are spotted onto the chip 20 on the lower side of the preceding spots at distances therefrom smaller than the distance (pitch) P between the pins 31 (e.g., P/4) as shown in FIG. 4c.

The procedure described above is repeated until the specific binding substances 11 in all the ninety-six holes 10a are spotted onto the chip 20 as shown in FIG. 4D.

In the conventional microarray chip manufacturing apparatus, the picking pins must be cleaned and dried each time they spot four specific binding substances. This means that cleaning and drying must be repeated twenty-four times four a chip 20 bearing thereon ninety-six (96) specific binding substances 11 (96/4=24) and three hundred and eighty-four (384) times for a chip 20 bearing thereon one thousand five hundred and thirty-six (1536) specific binding substances 11 (1536/4=384). The operation of cleaning and drying the picking pins requires a long time and deteriorates the efficiency of the spotting.

Further, the preceding specific binding substances 11 adhering to the picking pins cannot be perfectly cleaned, which gives rise to a problem that there is fear that the next specific binding substances 11 can be contaminated by the preceding specific binding substances.

SUMMARY OF THE INVENTION

In view of the foregoing observations and description, the primary object of the present invention is to provide a microarray chip manufacturing apparatus which can spot specific binding substances onto a chip in a shorter time.

The microarray chip manufacturing apparatus in accordance with the present invention is characterized in that the spaces among the picking means (e.g., picking pins, picking nozzles or the like) are changed when the picking means spot specific binding substances from those when the picking means pick the specific binding substances.

That is, in accordance with the present invention, there is provided a microarray chip manufacturing apparatus comprising a plurality of picking means which pick specific binding substances linearly or two-dimensionally arranged at first spaces and spot the specific binding substances onto a flat chip at second spaces narrower than the first spaces, wherein the improvement comprises that the picking means are movable so that the spaces among the picking means can be switched between said first spaces and said second spaces, and a space switching means switches the spaces among the picking means to said first spaces when the picking means pick the specific binding substances and to said second spaces when the picking means spot the specific binding substances onto the chip.

The specific binding substances may be, for instance, organism-originating substances such as cDNAs, and may be held in holes formed on a microtiter plate arranged linearly or two-dimensionally.

When the specific binding substances are held on a microtiter plate, the first spaces may be, for instance, about 1 mm to 10 mm and the second spaces may be, for instance, about 100 µm to 500 µm.

The flat chip is a substrate such as of a membrane filter or a slide glass which is spotted with the specific binding substances to form a microarray chip.

The space switching means may be of any structure so long as it can switch the spaces among the picking means between said first spaces and said second spaces. For example, the space switching means may comprise bellows connecting the picking means and a means for linearly or two-dimensionally expanding and contracting the bellows.

It is preferred that the picking means be provided in the same number as the number of the specific binding substances so that all the specific binding substances can be spotted onto the chip in one action.

In the microarray chip manufacturing apparatus of the resent invention, by switching the spaces among the picking means to the first spaces, equal to the spaces at which the specific binding substances are arranged, when the picking means pick the specific binding substances and to the second spaces, at which the specific binding substances are to be spotted onto the chip, when the picking means spot the specific binding substances onto the chip, a larger number of specific binding substances can be spotted at one time, whereby the time required to spot the specific binding substances can be shortened and at the same time, contamination of the specific binding substances with those spotted previously due to repeated use of the same picking means can be suppressed.

Further, when the picking means are provided in the same number as the number of the specific binding substances, all the specific binding substances can be spotted onto the chip at one time, whereby the time required to spot the specific binding substances can be further shortened and at the same time, contamination of the specific binding substances with those spotted previously, which can occur when the same picking means are repeatedly used, can be prevented.

BRIEF DESCRIPTION OF THE DRAWINGS

FIG. 2 is a perspective view showing in detail the space switching means employed in the microarray chip manufacturing apparatus shown in FIG. 1, FIG. 5 is a perspective view showing a microarray chip, and FIG. 6 is a perspective view showing a modification of the microarray chip manufacturing apparatus shown in FIG. 1 where the space switching means comprises bellows.

DESCRIPTION OF THE PREFERRED EMBODIMENTS

Figure 1:
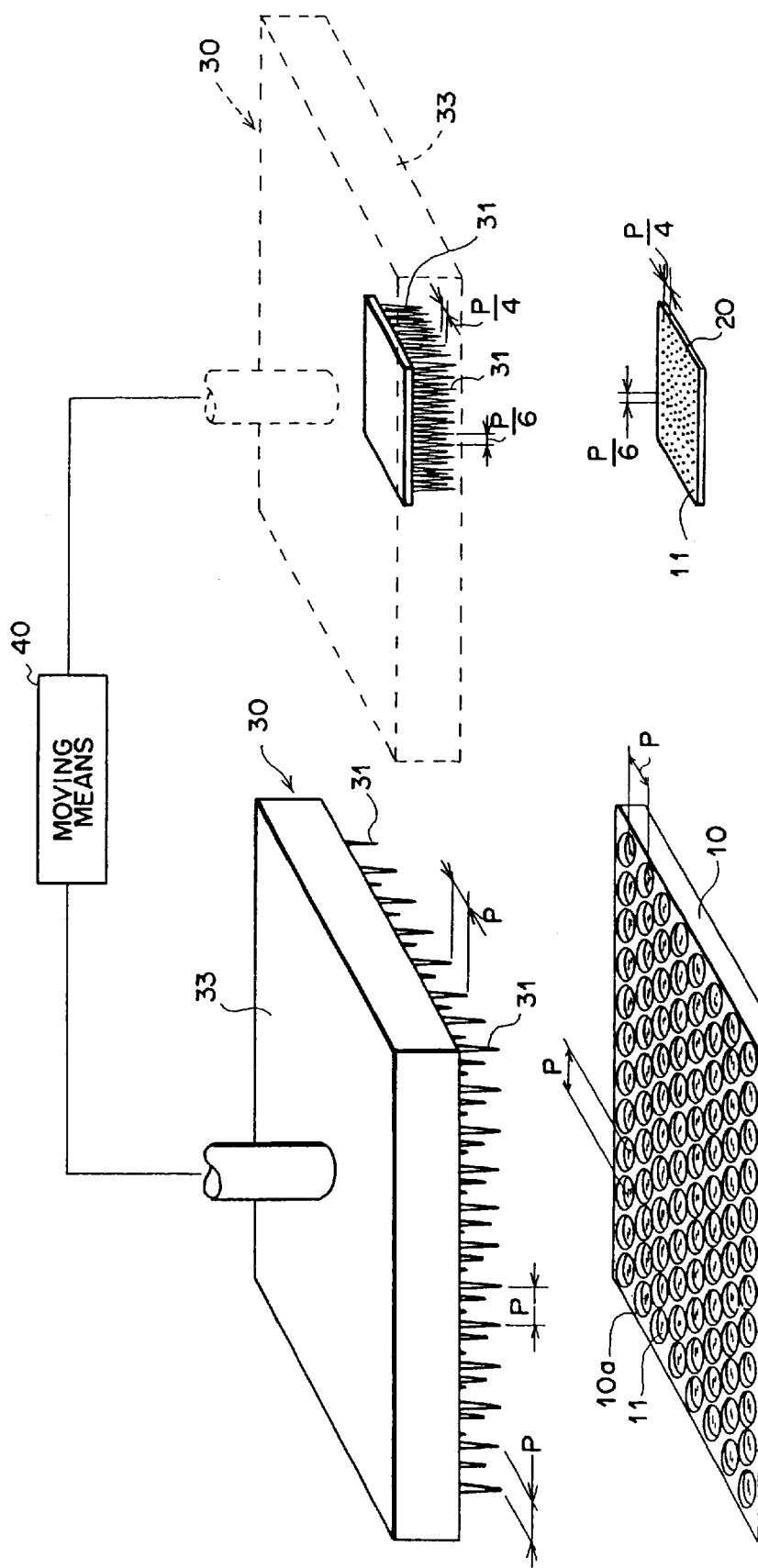
FIG. 1 is a perspective view of a microarray chip manufacturing apparatus in accordance with a first embodiment of the present invention.
Figure 3:
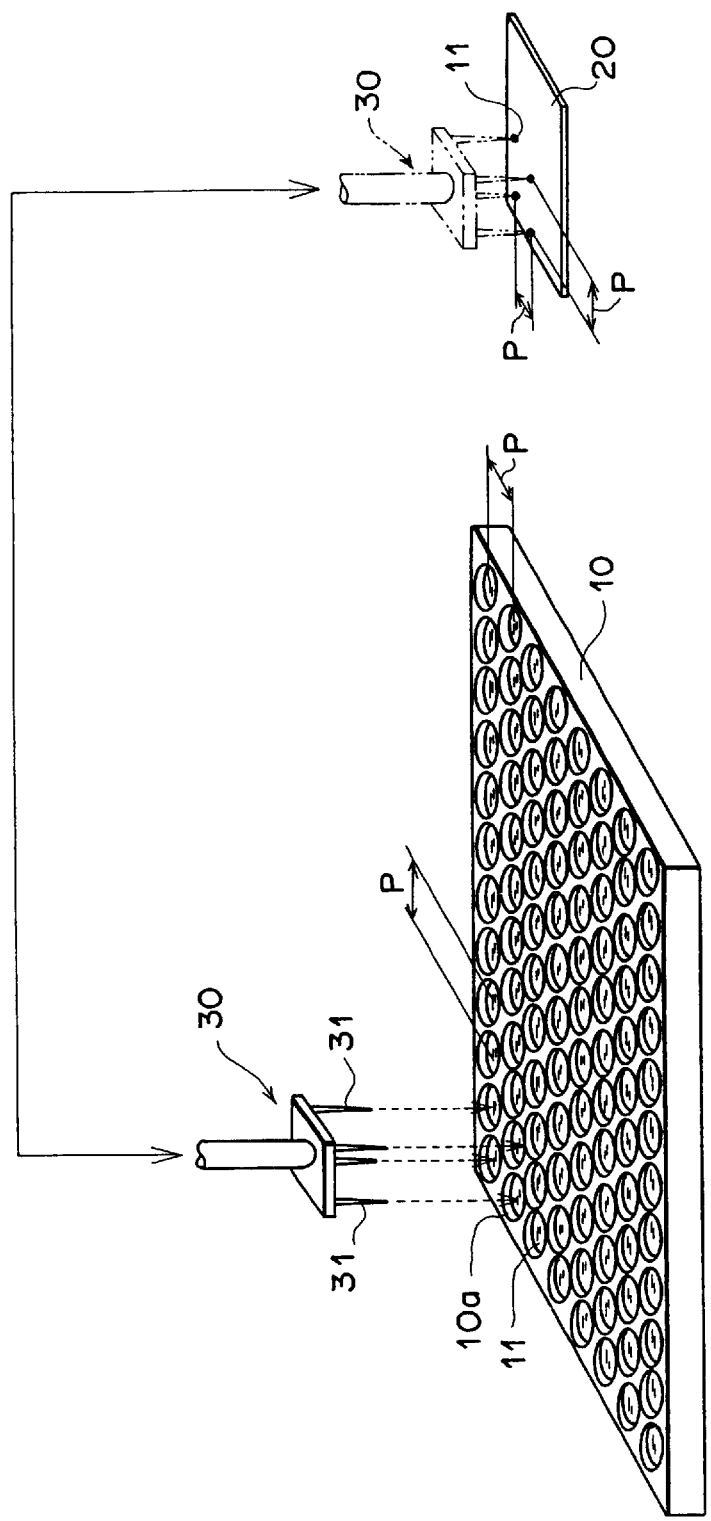
FIG. 3 is a perspective view showing a microarray chip manufacturing apparatus in accordance with the prior art.
Figure 4A:
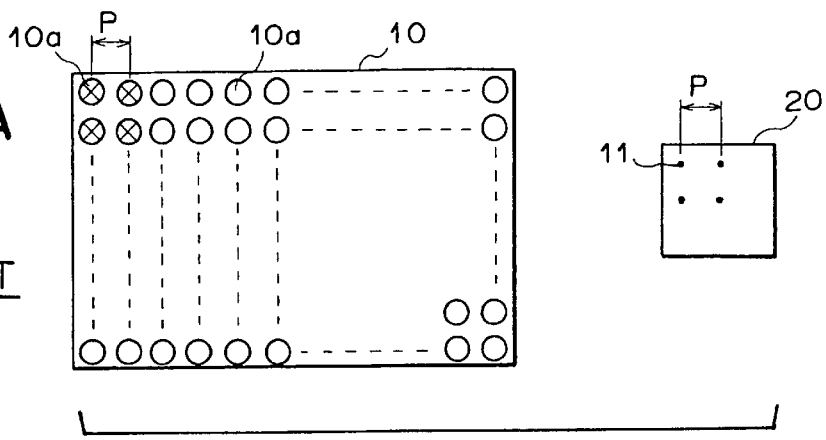
FIGS. 4A to 4D are views for illustrating operation of the conventional microarray chip manufacturing apparatus.
Figure 4B:
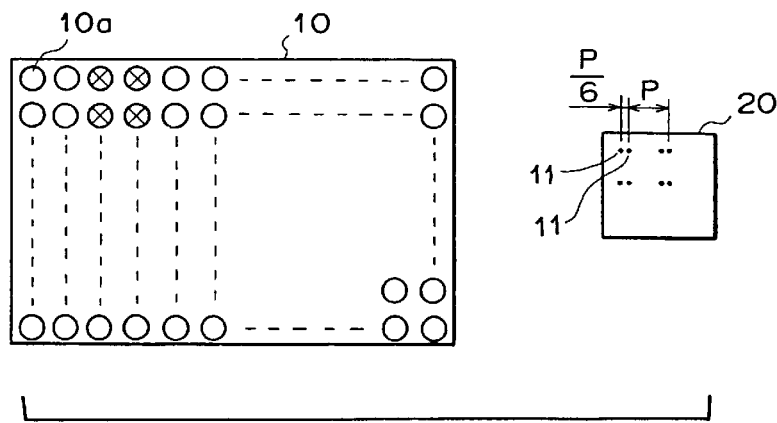
Figure 4C:
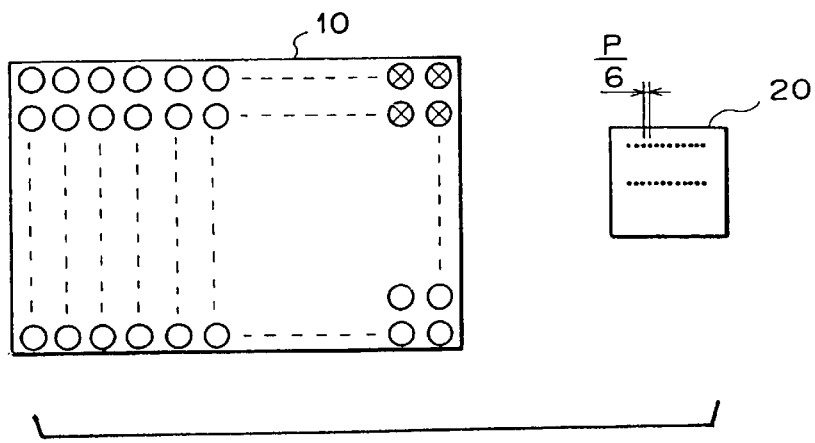
Figure 4D:
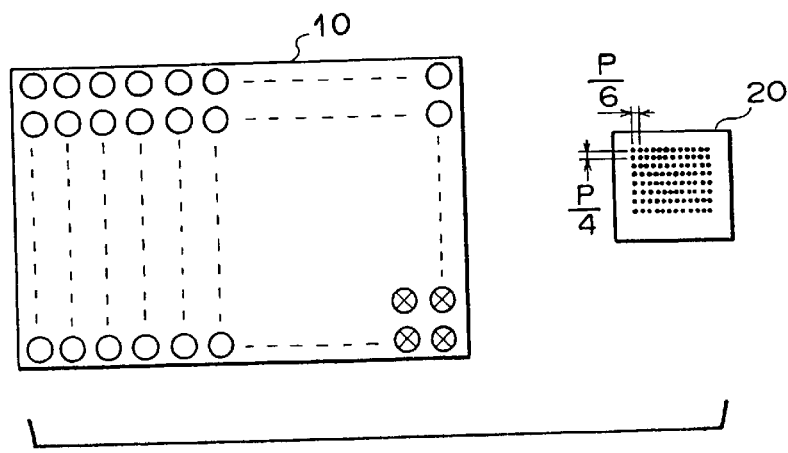

In FIG. 1, a microarray chip manufacturing apparatus in accordance with an embodiment of the present invention comprises a spot head 30 on which a plurality of picking pins 31 which pick specific binding substances 11 held in specific binding substance holes 10a on a microtiter plate 10 and spot the specific binding substances 11 onto a slide glass 20 are supported, and a moving means 40 for moving the spot head 30 between the microtiter plate 10 and the slide glass 20. The specific binding substance holes 10a are ninety-six in number and are two-dimensionally arranged on the microtiter plate 10 at spaces of P, eight in the longitudinal direction of plate 10 and twelve in the transverse direction of the same (8×12).

The picking pins 31 are the same as the holes 10a in number (8×12=96) and the spaces among the pins 31 are variable. The spaces among the pins 31 are variable between P and P/6 in the transverse direction of the plate 10 and between P and P/4 in the longitudinal direction of the same.

The spot head 30 is provided with a space switching means 33 which switches the spaces among the pins 31. The space switching means 33 switches the spaces among the pins 31 to P in both the longitudinal and transverse directions of the plate 10 when the pin 31 pick the specific binding substances 11 from the plate 10 and to P/6 and P/4 respectively in the transverse and longitudinal directions of the plate 10 when the pins 31 spot the specific binding substances 11 onto the slide glass 20.

FIG. 2 shows the space switching means 33. As shown in FIG. 2, the space switching means 33 is like a mechanism for opening and shutting a window shade. In FIG. 2, some of the pins 31 (indicated at 31a, 31b, 31c ... in FIG. 2) and some elements are eliminated for the purpose of simplicity.

In FIG. 2, pins 31a, 31b and 31c on a transverse line are respectively fixed to sliders 33d, 33e and 33f which are mounted on a support shaft 33a in the transverse direction to be slidable along the shaft 33a. A threaded rod 33b extends through the sliders 33d, 33e and 33f in parallel to the support shaft 33a. A guide slider 33c is mounted on the support shaft 33a at the right side end portion thereof to be slidable along the support shaft 33a. The guide slider 33c has a threaded hole in mesh with the threaded rod 33b so that the guide slider 33c is moved along the support shaft 33a in response to revolution of the threaded rod 33b. The guide slider 33c and the slider 33d are connected by a chain 33g, the sliders 33d and 33e are connected by a chain 33h and the sliders 33e and 33f are connected by a chain 33i.

Support shafts 33j and 33k similar to the support shaft 33a are provided and the support shafts 33a, 33j and 33k are supported by guide rails 34a and 34b at their opposite ends to be movable in the direction perpendicular to the longitudinal direction thereof. The support shafts 33a, 33j and 33k are moved along the guide rails 34a and 34b in parallel to each other by an electric motor not shown.

When the chains 33g, 33h and 33i are tensioned straight, the spaces between the pins 31a and 31b and 31b and 31c are P, and the spaces between the support shafts 33a and 33j and 33j and 33k are also P.

When the threaded rod 33b is revolved by an electric motor (not shown) in one direction, the guide slider 33c is moved leftward and pushes slider 33d leftward so that the slider 33d pushes leftward the slider 33e to bring the slider 33e in contact with the slider 33f. Finally, the sliders 33c, 33d, 33e and 33f are held in contact with each other side by side. In this state, the spaces between the pins 31a and 31b and between the pins 31b and 31c are equal to P/6 and the chains 33g, 33h and 33i hang down. The spaces between the pins supported by the support shafts 33j and 33k are made equal to P/6 in the same manner.

Further the spaces between the pins in the longitudinal direction are made equal to P/4 by moving the support shafts 33j and 33k toward the support shaft 33a along the guide shafts 34a and 34b by the electric motor (not shown).

When the electric motor is reversed to move the support shafts 33j and 33k away from the support shaft 33a, the spaces between the pins in the longitudinal direction are returned to P. Further, when the threaded rod 33b is reversed, the guide slider 33c is moved rightward away from the slider 33d, and when the chain 33g is tensioned straight (the space between the guide slider 33c and the slider 33d becomes P), the slider 33d is pulled rightward. In this manner, when all the chains 33g, 33h and 33i are tensioned straight, the guide slide 33c is stopped, whereby the spaces between the pins in the transverse direction are returned to P.

Though, in this embodiment, the adjacent pins are connected by chains, the adjacent pins may be connected by bellows 33z as shown in FIG. 6, or by X-shaped movable links.

Operation of the microarray chip manufacturing apparatus of the embodiment will be described, hereinbelow.

After the spaces P among the pins 31 are held at P by the space switching means 33, the moving means 40 moves the spot head 30 to above the microtiter plate 10 so that the pins 31 on the head 30 are respectively aligned with the specific binding substance holes 10a of the plate 10.

Then the moving means 40 moves downward the head 30 so that the pins 31 are inserted into the holes 10a, whereby the specific binding substances 11 in the holes 10a adhere to the pins 31. Then the moving means 40 moves upward the head 30 and moves the head 30 to above the slide glass 20.

Then the space switching means 33 switches the spaces among the pins 31 in the longitudinal direction to P/4 and the spaces among the pins 31 in the transverse direction to P/6. In this state, all the pins 31 on the head 30 are held in the area of the slide glass 20, which is 2 cm×2 cm in size.

Then the moving means 40 moves downward the head 30 so that the pins 31 are brought into contact with the surface of the slide glass 20 and the specific binding substances 11 on the pins 31 are spotted onto the slide glass 20. After the specific binding substances 11 are spotted onto the slide glass 20, the moving means 40 moves upward the head 30 away from the slide glass 20.

As can be understood from the description above, in the microarray chip manufacturing apparatus of this embodiment, by switching the spaces among the picking pins 31 to the spaces equal to the spaces P, at which the specific binding substances 11 are arranged, when the picking pins 31 pick the specific binding substances 11 and to the spaces at which the specific binding substances 11 are to be spotted onto the slide glass 20 when the picking pins 31 spot the specific binding substances 11 onto the slide glass 20 (to P/4 in the longitudinal direction and to P/6 in the transverse direction), a larger number of specific binding substances 11 can be spotted at one time, whereby the time required to spot the specific binding substances can be shortened.

Further, in the apparatus in accordance with this particular embodiment, since the picking pins 31 are provided in the same number as the number of the specific binding substances 11, all the specific binding substances 11 can be spotted onto the slide glass 20 at one time, whereby contamination of the specific binding substances 11 with those spotted previously, which can occur when the same picking pins 31 are repeatedly used without perfectly cleaning the pins 31, can be prevented.

In addition, all of the contents of japanese patent application no. 11(1999)-279090 are incorporated into this specification by reference.

What is claimed is:

1. A microarray chip manufacturing apparatus comprising a plurality of picking means which pick specific binding substances linearly or two-dimensionally arranged at first spaces and spot the specific binding substances onto a flat chip at second spaces narrower than the first spaces, wherein the improvement comprises that the picking means are movable so that the spaces among the picking means can be switched between said first spaces and said second spaces, and a space switching means switches the spaces among the picking means to said first spaces when the picking means pick the specific binding substances and to said second spaces when the picking means spot the specific binding substances onto the chip.

2. A microarray chip manufacturing apparatus as defined in claim 1 in which the specific binding substances are organism-originating substances.

3. A microarray chip manufacturing apparatus as defined in claim 2 in which the specific binding substances are cDNAs.

4. A microarray chip manufacturing apparatus as defined in claim 1 in which the picking means are provided in the same number as the number of the specific binding substances.

5. A microarray chip manufacturing apparatus comprising a plurality of picking means for picking specific binding substances two-dimensionally arranged at first longitudinal and horizontal spaces and spot the specific binding substances onto a flat chip at second longitudinal and horizontal spaces, wherein the improvement comprises that the picking means are movable so that the spaces among the picking means can be switched between said first longitudinal and horizontal spaces and said second longitudinal and horizontal spaces, and a space switching means for switching the spaces among the picking means to said first longitudinal and horizontal spaces when the picking means pick the specific binding substances and to said second longitudinal and horizontal spaces when the picking means spot the specific binding substances onto the chip.

6. The microarray chip manufacturing apparatus as defined in claim 5, wherein the second longitudinal spaces are substantially smaller than the first longitudinal spaces.

7. The microarray chip manufacturing apparatus as defined in claim 5, wherein the second horizontal spaces are substantially smaller than the first horizontal spaces.

8. The microarray chip manufacturing apparatus as defined in claim 5, wherein the second longitudinal spaces are different from the second horizontal spaces.

\* \* \* \* \*